US012728087B2

(12) United States Patent
Suthiwangcharoen et al.

(10) Patent No.: US 12,728,087 B2
(45) **Date of Patent: *Sep. 8, 2026**

(54) HAIR CONDITIONER

(71) Applicants: Dow Global Technologies LLC, Midland, MI (US); Rohm and Haas Company, Collegeville, PA (US); Dow Silicones Corporation, Midland, MI (US)

(72) Inventors: Nisaraporn Suthiwangcharoen, Midland, MI (US); Lyndsay M. Leal, Spring City, PA (US); Michaeleen Pacholski, Collegeville, PA (US); Shannon Golden, Saginaw, MI (US); Emmett M. Partain, III, Bound Brook, NJ (US); Lu Bai, Novi, MI (US); Daniel S. Miller, Phoenixville, PA (US)

(73) Assignees: Dow Global Technologies LLC, Midland, MI (US); Dow Silicones Corporation, Midland, MI (US); ROHM AND HAAS COMPANY, Collegeville, PA (US)

( * ) Notice: Subject to any disclaimer, the term of this patent is extended or adjusted under 35 U.S.C. 154(b) by 241 days.

This patent is subject to a terminal disclaimer.

(21) Appl. No.: 18/261,515

(22) PCT Filed: Mar. 9, 2022

(86) PCT No.: PCT/US2022/019469
§ 371 (c)(1),
(2) Date: Jul. 14, 2023

(87) PCT Pub. No.: WO2022/203865
PCT Pub. Date: Sep. 29, 2022

(65) Prior Publication Data

US 2024/0091124 A1 Mar. 21, 2024

Related U.S. Application Data

(60) Provisional application No. 63/164,064, filed on Mar. 22, 2021.

(51) Int. Cl.
*A61K 8/73* (2006.01)
*A61Q 5/12* (2006.01)

(52) U.S. Cl.
CPC .................. *A61K 8/73* (2013.01); *A61Q 5/12* (2013.01); *A61K 2800/48* (2013.01); *A61K 2800/524* (2013.01); *A61K 2800/5426* (2013.01)

(58) Field of Classification Search
None
See application file for complete search history.

(56) References Cited

U.S. PATENT DOCUMENTS

| | | | | |
|---|---|---|---|---|
| 4,411,891 | A | 10/1983 | Mizutani et al. | |
| 4,774,075 | A * | 9/1988 | Lang ...................... | A61K 8/416 510/423 |
| 8,518,387 | B2 | 8/2013 | Drovetskaya et al. | |
| 10,633,683 | B2 | 4/2020 | Paullin et al. | |

(Continued)

FOREIGN PATENT DOCUMENTS

| | | |
|---|---|---|
| CN | 106511133 | 3/2017 |
| DE | 10018158 | 10/2001 |

(Continued)

OTHER PUBLICATIONS

Machine Translation of JP2000159642 (Year: 2000).*

(Continued)

*Primary Examiner* — Jennifer A Berrios
(74) *Attorney, Agent, or Firm* — Thomas S. Deibert

(57) ABSTRACT

A hair conditioner formulation is provided, comprising: a dermatologically acceptable vehicle; and a conditioning polymer, wherein the conditioning polymer is a cationic dextran polymer, comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer wherein is a pendent oxygen on the dextran polymer; wherein X is a divalent linking group bonding the quaternary ammonium moiety to the pendent oxygen on the dextran polymer; wherein each $R^2$ is independently selected N from the group consisting of a $C_{1-3}$ alkyl group; and wherein each $R^3$ is independently selected from the group consisting of a linear or branched $C_{4-16}$ alkyl group.

(A)

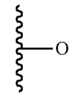

10 Claims, No Drawings

(56) References Cited

U.S. PATENT DOCUMENTS

| | | | |
|---|---|---|---|
| 10,716,748 | B2 | 7/2020 | Gonzalez et al. |
| 10,874,598 | B2 | 12/2020 | Yang et al. |
| 2008/0003192 | A1 | 1/2008 | Modi |
| 2010/0093584 | A1 | 4/2010 | Brand et al. |
| 2010/0247472 | A1 | 9/2010 | Sau |
| 2011/0177017 | A1 | 7/2011 | Coffindaffer et al. |
| 2014/0154200 | A1 | 6/2014 | Lizarraga et al. |
| 2015/0098920 | A1 | 4/2015 | Stella et al. |
| 2015/0203598 | A1 | 7/2015 | Landschutze et al. |
| 2018/0237816 | A1 | 8/2018 | Paullin et al. |
| 2020/0323758 | A1 | 10/2020 | Karagianni et al. |
| 2024/0294849 | A1 | 9/2024 | Miller et al. |

FOREIGN PATENT DOCUMENTS

| | | |
|---|---|---|
| EP | 2119428 | 11/2009 |
| EP | 3486356 | 5/2019 |
| JP | 10279449 | 10/1998 |
| JP | 11322555 | 11/1999 |
| JP | 2000159642 | 6/2000 |
| JP | 2000319139 | 11/2000 |
| JP | 2001220323 | 8/2001 |
| JP | 3720964 | 11/2005 |
| JP | 2009062281 | 3/2009 |
| JP | 4712222 | 6/2011 |
| WO | 2010009938 | 1/2010 |
| WO | 2010089228 | 8/2010 |
| WO | 2014047099 | 3/2014 |
| WO | 2017174678 | 10/2017 |
| WO | 2021194804 | 9/2021 |
| WO | 2021194805 | 9/2021 |
| WO | 2021194807 | 9/2021 |
| WO | 2021194809 | 9/2021 |

OTHER PUBLICATIONS

Jachowicz, J. 'Cosmetic Raw Material Analysis and Quality,' 2004, p. 16. International Federation of the Societies of Cosmetic Chemists (Year: 2004).*

University of Cambridge, 'Molecular weight,' webpage <https://www.doitpoms.ac.uk/tlplib/polymerbasics/mw.php>, pp. 1-4, May 3, 2011, retrieved from Internet Archive Wayback Machine <https://web.archive.org/web/20110503191252/https://www.doitpoms.ac.uk/tlplib/polymerbasics/mw.php> (Year: 2011).*

Mintel, "Chinese Medicine Anti-Dandruff & Olive Moisturising Shampoo", Bawang Cosmetic, 2015, Database GNPD, CN.

Mintel, "Refresh Mint Cool Body Wash Gel", Bawang Cosmetic, 2015, Database GNPD, CN.

Sibilia, "A Guide to Materials Characterization and Chemical Analysis", VCH, 1988, pp. 81-84.

Stanciu "Influence of dextran hydrogel characteristics on adsorption capacity for anionic dyes", Carbohydrate Polymers, 2018, vol. 199, pp. 75-83, Applied Science Publishers, Ltd Barking, GB.

Yau "Modern Size Exclusion Chromatography", 1979, Wiley-Interscience.

* cited by examiner

HAIR CONDITIONER

The present invention relates to a hair conditioner formulation. In particular, the present invention relates to a hair conditioner formulation containing a dermatologically acceptable vehicle; and a conditioning polymer, wherein the conditioning polymer is a cationic dextran polymer, comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer (A)

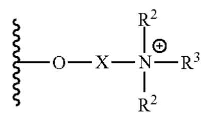

wherein

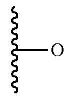

is a pendent oxygen on the dextran polymer; wherein X is a divalent linking group bonding the quaternary ammonium moiety to the pendent oxygen on the dextran polymer; wherein each $R^2$ is independently selected from the group consisting of a $C_{1-3}$ alkyl group; and wherein each $R^3$ is independently selected from the group consisting of a linear or branched $C_{4-16}$ alkyl group.

Conventional hair conditioners are popular with consumers for treating hair. Silicone based conditioning agents are the most commonly used conditioning agent in hair conditioner formulations. However, there are growing concerns among some consumers regarding the persistence and potential toxicity of certain silicone based conditioning agents or trace compounds incorporated with such silicone based conditioning agents in the environment, particularly for D4 and D5 conditioners. Accordingly, there has been a growing interest in the development of silicone-free alternative conditioning agents for use in hair conditioner formulations.

In U.S. Pat. No. 5,879,670, Melby et al disclose a non-silicon containing amphyolyte polymer for use as a conditioning agent for treatment of a keratin-containing substrate. In particular, Melby et al disclose novel conditioning polymer containing (meth)acrylamidopropyltrimethyl ammonium chloride, meth(acrylic acid) or 2-(meth)acrylamido-2-methylpropane sulfonic acid and, optionally, a $C_{1-22}$ alkyl (meth)acrylate and the use thereof in a cosmetically acceptable medium for the treatment of a keratin-containing substrate.

Notwithstanding, there is a continuing need for new hair conditioning agents that provide conditioning benefits. There is also a continuing need for new hair conditioning agents having an increased natural origin index (ISO16128) when compared with conventional hair conditioning agents.

The present invention provides a hair conditioner formulation, comprising: a dermatologically acceptable vehicle; and a conditioning polymer, wherein the conditioning polymer is a cationic dextran polymer, comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer (A)

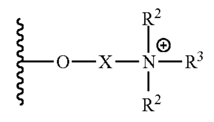

wherein

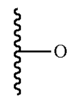

is a pendent oxygen on the dextran polymer; wherein X is a divalent linking group bonding the quaternary ammonium moiety to the pendent oxygen on the dextran polymer; wherein each $R^2$ is independently selected from the group consisting of a $C_{1-3}$ alkyl group; and wherein each $R^3$ is independently selected from the group consisting of a linear or branched $C_{4-16}$ alkyl group.

The present invention provides a method of conditioning mammalian hair, comprising: selecting a hair conditioner formulation of the present invention; and applying the hair conditioner formulation to mammalian hair.

DETAILED DESCRIPTION

We have surprisingly found that a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer (A)

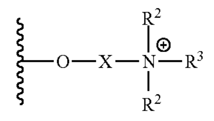

wherein

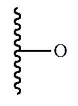

is a pendent oxygen on the dextran polymer; wherein X is a divalent linking group bonding the quaternary ammonium moiety to the pendent oxygen on the dextran polymer; wherein each $R^2$ is independently selected from the group consisting of a $C_{1-3}$ alkyl group; and wherein each $R^3$ is independently selected from the group consisting of a linear or branched $C_{4-16}$ alkyl group; acts as a conditioning polymer that effectively restores hydrophobicity to damaged hair and reduces the force required to comb treated hair.

Unless otherwise indicated, ratios, percentages, parts, and the like are by weight.

As used herein, unless otherwise indicated, the phrase "molecular weight" or $M_W$ refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the hair conditioner formulation of the present invention is selected from the group consisting of a conditioning shampoo formulation, a rinse off conditioner formulation and a leave on conditioner formulation. More preferably, the hair conditioner formulation of the present invention is selected from the group consisting of a rinse off conditioner formulation and a leave on conditioner formulation. Most preferably, the hair conditioner formulation of the present invention is a rinse off conditioner formulation.

Preferably, the hair conditioner formulation of the present invention, comprises: a dermatologically acceptable vehicle (preferably, wherein the hair conditioner formulation comprises 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle); and a conditioning polymer (preferably, wherein the hair conditioner formulation comprises 0.1 to 1 wt % (preferably, 0.15 to 0.75 wt %; more preferably, 0.2 to 0.5 wt %; most preferably, 0.25 to 0.4 wt %), based on weight of the hair conditioner formulation, of a tertiary amine functionalized dextran polymer); wherein the conditioning polymer is a cationic dextran polymer, comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer (A)

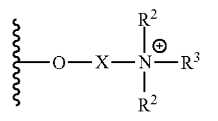

wherein

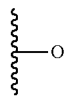

is a pendent oxygen on the dextran polymer; wherein X is a divalent linking group bonding the quaternary ammonium moiety to the pendent oxygen on the dextran polymer; wherein each $R^2$ is independently selected from the group consisting of a $C_{1-3}$ alkyl group (preferably, a $C_{1-3}$ alkyl group; more preferably, a $C_{1-2}$ alkyl group; most preferably, a methyl group); and wherein each $R^3$ is independently selected from the group consisting of a linear or branched $C_{4-16}$ alkyl group (preferably, a linear or branched $C_{6-14}$ alkyl group; more preferably, a linear or branched $C_{8-12}$ alkyl group; still more preferably, a linear or branched $C_8$ alkyl group and a linear or branched $C_{12}$ alkyl group; most preferably, a linear $C_8$ alkyl group and a linear $C_{12}$ alkyl group).

Preferably, the hair conditioner formulation of the present invention is a liquid formulation. More preferably, the hair conditioner formulation of the present invention is an aqueous liquid formulation.

Preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle. More preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle comprises water. Still more preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle is selected from the group consisting of water and an aqueous $C_{1-4}$ alcohol mixture. Most preferably, the hair conditioner formulation of the present invention, comprises: 50 to 99.9 wt % (preferably, 75 to 99.85 wt %; more preferably, 80 to 99.8 wt %; most preferably, 90 to 99.75 wt %), based on weight of the hair conditioner formulation, of a dermatologically acceptable vehicle; wherein the dermatologically acceptable vehicle is water.

Preferably, the water used in the hair conditioner formulation of the present invention is at least one of distilled water and deionized water. More preferably, the water used in the hair conditioner formulation of the present invention is distilled and deionized.

Preferably, the hair conditioner formulation of the present invention comprises 0.1 to 1 wt % (preferably, 0.15 to 0.75 wt %; more preferably, 0.2 to 0.5 wt %; most preferably, 0.25 to 0.4 wt %), based on weight of the hair conditioner formulation, of a conditioning polymer; wherein the conditioning polymer is a cationic dextran polymer, comprising a dextran polymer functionalized with quaternary ammonium groups; wherein the dextran polymer has a weight average molecular weight of 50,000 to 3,000,000 Daltons.

Preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons). More preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); and the dextran polymer is a branched chain dextran polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages. Most preferably, the dextran polymer has a weight average molecular weight of 50,000 to 3,000,000 Daltons (preferably, 100,000 to 2,000,000 Daltons; more preferably, 125,000 to 1,000,000 Daltons; still more preferably, 130,000 to 650,000 Daltons; most preferably, 145,000 to 525,000 Daltons); and the dextran polymer is a branched chain dextran polymer comprising a plurality of glucose structural units; wherein 90 to 98 mol % (preferably, 92.5 to 97.5 mol %; more preferably, 93 to 97 mol %; most preferably, 94 to 96 mol %) of the glucose structural units are connected by α-D-1,6 linkages and 2 to 10 mol % (preferably, 2.5 to 7.5 mol %; more preferably, 3 to 7 mol %; most preferably, 4 to 6 mol %) of the glucose structural units are connected by α-1,3 linkages according to formula I (I)

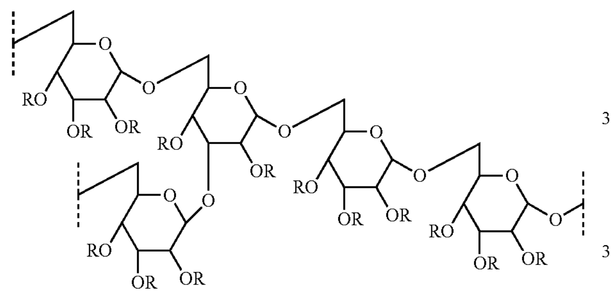

wherein R is selected from a hydrogen, a $C_{1-4}$ alkyl group and a hydroxy $C_{1-4}$ alkyl group; and wherein the average branch off the dextran polymer backbone is ≤3 anhydroglucose units.

Preferably, the dextran polymer contains less than 0.01 wt %, based on weight of the dextran polymer, of alternan. More preferably, the dextran polymer contains less than 0.001 wt %, based on weight of the dextran polymer, of alternan. Most preferably, the dextran polymer contains less than the detectable limit of alternan.

Preferably, the hair conditioner formulation of the present invention comprises 0.05 to 5 wt % (preferably, 0.1 to 2 wt %; more preferably, 0.15 to 1 wt %; most preferably, 0.2 to 0.5 wt %), based on weight of the hair conditioner formulation, of a conditioning polymer; wherein the conditioning polymer is a cationic dextran polymer comprising a dextran polymer functionalized with quaternary ammonium groups; wherein the quaternary ammonium groups are selected from the group consisting of quaternary ammonium moieties of formula (A) bound to a pendent oxygen on the dextran polymer (A)

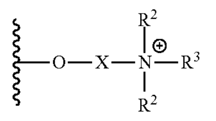

wherein

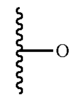

is a pendent oxygen on the dextran polymer; wherein X is a divalent linking group bonding the quaternary ammonium moiety to the pendent oxygen on the dextran polymer (preferably, wherein X is selected from divalent hydrocarbon groups, which may optionally be substituted (e.g., with a hydroxy group, an alkoxy group, an ether group); more preferably, wherein X is a $—CH_2CH(OR^4)CH_2—$ group; wherein $R^4$ is selected from the group consisting of a hydrogen and a $C_{1-4}$ alkyl group (preferably, a hydrogen); most preferably, X is a $—CH_2CH(OH)CH_2—$ group); wherein each $R^2$ is independently selected from the group consisting of a $C_{1-4}$ alkyl group (preferably, a $C_{1-3}$ alkyl group; more preferably, a $C_{1-2}$ alkyl group; most preferably, a methyl group); wherein each $R^3$ is independently selected from the group consisting of a linear or branched $C_{4-16}$ alkyl group (preferably, a linear or branched $C\text{-}_{6-14}$ alkyl group; more preferably, a linear or branched $C_{8-12}$ alkyl group; still more preferably, a linear or branched $C_8$ alkyl group and a linear or branched $C_{12}$ alkyl group; most preferably, a linear $C_8$ alkyl group and a linear $C_{12}$ alkyl group). More preferably, the hair conditioner formulation of the present invention comprises 0.05 to 5 wt % (preferably, 0.1 to 2 wt %; more preferably, 0.15 to 1 wt %; most preferably, 0.2 to 0.5 wt %), based on weight of the hair conditioner formulation, of a conditioning polymer, wherein the conditioning polymer is a cationic dextran polymer comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (B) bound to a pendent oxygen on the dextran polymer (B)

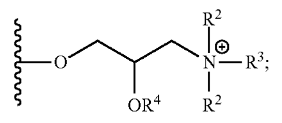

wherein

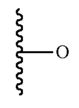

is a pendent oxygen on the dextran polymer; wherein each $R^2$ is independently selected from the group consisting of a $C_{1-4}$ alkyl group (preferably, a $C_{1-3}$ alkyl group; more preferably, a $C_{1-2}$ alkyl group; most preferably, a methyl group); wherein each $R^3$ is independently selected from the group consisting of a linear or branched $C_{4-16}$ alkyl group (preferably, a linear or branched $C_{6-14}$ alkyl group; more preferably, a linear or branched $C_{8-12}$ alkyl group; still more preferably, a linear or branched $C_8$ alkyl group and a linear or branched $C_{12}$ alkyl group; most preferably, a linear $C_8$ alkyl group and a linear $C_{12}$ alkyl group). Most preferably, the hair conditioner formulation of the present invention comprises 0.05 to 5 wt % (preferably, 0.1 to 2 wt %; more preferably, 0.15 to 1 wt %; most preferably, 0.2 to 0.5 wt %), based on weight of the hair conditioner formulation, of a conditioning polymer, wherein the conditioning polymer is a cationic dextran polymer comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (B) bound to a pendent oxygen on the dextran polymer; wherein each $R^2$ is a methyl group; wherein each $R^3$ is independently selected from the group consisting of a linear $C_8$ alkyl group and a linear $C_{12}$ alkyl group; and $R^4$ is a hydrogen.

Preferably, the conditioning polymer has a Kjeldahl nitrogen content, TKN, of 0.5 to 5.0 wt % (preferably, 0.75 to 4 wt %; more preferably, 1 to 3.5 wt %; most preferably, 1.5 to 3.0 wt %) measured using a Buchi KjelMaster K-375 automated analyzer, corrected for volatiles and ash measured as described in ASTM method D-2364.

Preferably, the conditioning polymer comprises <0.001 meq/gram (preferably, <0.0001 meq/gram; more preferably, <0.00001 meq/gram; most preferably, <detectable limit) of aldehyde functionality.

Preferably, the conditioning polymer comprises <0.1% (preferably, <0.01%; more preferably, <0.001%; most preferably, <detectable limit), of the linkages between individual glucose units in the conditioning polymer are β-1,4 linkages.

Preferably, the conditioning polymer comprises <0.1% (preferably, <0.01%; more preferably, <0.001%; most preferably, <detectable limit), of the linkages between individual glucose units in the conditioning polymer are β-1,3 linkages.

Preferably, the conditioning polymer comprises <0.001 meq/gram (preferably, <0.0001 meq/gram; more preferably, <0.00001 meq/gram; most preferably, <detectable limit) of silicone containing functionality.

Preferably, the hair conditioner formulation of the present invention contains <0.01 wt % (preferably, <0.001 wt %; more preferably, <0.0001 wt %; most preferably, <detectable limit), based on weight of the hair conditioner formulation of a dermatologically acceptable oil. More preferably, the hair conditioner formulation of the present invention contains <0.01 wt % (preferably, <0.001 wt %; more preferably, <0.0001 wt %; most preferably, <detectable limit), based on weight of the hair conditioner formulation of a dermatologically acceptable oil; wherein the dermatologically acceptable oil is selected from the group consisting of hydrocarbon oils (e.g., mineral oil, petroleum jelly, polyisobutene, hydrogenated polyisobutene, hydrogenated polydecene, polyisohexadecane; natural oils (e.g., caprylic and capric triglyceride, sunflower oil, soybean oil, coconut oil, argan oil, olive oil, almond oil); fragrance oils (e.g., limonene) and mixtures thereof.

Preferably, the hair conditioner formulation of the present invention contains <0.1 wt % (preferably, <0.001 wt %; more preferably, <0.0001 wt %; most preferably, <detectable limit), based on weight of the hair conditioner formulation, of silicones (e.g., polydimethylsiloxanes, dimethicone, cyclodimethicone).

Preferably, the hair conditioner formulation of the present invention contains <0.1 wt % (preferably, <0.001 wt %; more preferably, <0.0001 wt %; most preferably, <detectable limit), based on weight of the hair conditioner formulation, of silicon (Si) containing molecules.

Preferably, the hair conditioner formulation of the present invention, optionally, further comprises at least one additional ingredient selected from the group consisting of an antimicrobial agent/preservative (e.g., benzoic acid, sorbic acid, phenoxyethanol, methylisothiazolinone); a cleansing surfactant; a rheology modifier (e.g., PEG-150 pentaerythrityl tetrastearate); a soap; a colorant; pH adjusting agent; an antioxidant (e.g., butylated hydroxytoluene); a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, cationic polymeric polyols); a wax; a foaming agent; an emulsifying agent; a colorant; a fragrance; a chelating agent (e.g., tetrasodium ethylene diamine tetraacetic acid); a preservative (e.g., benzoic acid, sorbic acid, phenoxyethanol, methylisothiazolinone); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an antidandruff agent; a hair waving/straightening agent; a hair styling agent; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the hair conditioner formulation of the present invention, optionally, further comprises at least one additional ingredient selected from the group consisting of an antimicrobial agent/preservative (e.g., benzoic acid, sorbic acid, phenoxyethanol, methylisothiazolinone); a cleansing surfactant; a rheology modifier (e.g., PEG-150 pentaerythrityl tetrastearate); and a chelating agent (e.g., tetrasodium ethylene diamine tetraacetic acid). Most preferably, the hair conditioner formulation of the present invention, optionally, further comprises at least one additional ingredient selected from the group consisting of an antimicrobial agent/preservative mixture of phenoxyethanol and methylisothiazolinone; PEG-150 pentaerythrityl tetrastearate; tetrasodium ethylene diamine tetraacetic acid and a mixture of phenoxyethanol and methylisothiazolinone.

Preferably, the hair conditioner formulation of the present invention further comprises a dermatologically acceptable hair care cleansing surfactant. More preferably, the hair conditioner formulation of the present invention further comprises a dermatologically acceptable hair care cleansing surfactant, wherein the dermatologically acceptable hair care cleansing surfactant is selected from the group consisting of alkyl polyglucosides (e.g., lauryl glucoside, cocoglucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium lauryl ether sulfate (SLES)), sulfonates (e.g., sodium $C_{14-16}$ olefin sulfonate), succinates (e.g., disodium lauryl sulfosuccinate), fatty alkanolamides (e.g., cocamide monoethanolamine, cocamide diethanolamine, soyamide diethanolamine, lauramide diethanolamine, oleamide monoisopropanolamine, stearamide monoethanolamine, myristamide monoethanolamine, lauramide monoethanolamine, capramide diethanolamine, ricinoleamide diethanolamine, myristamide diethanolamine, stearamide diethanolamine, oleylamide diethanolamine, tallowamide diethanolamine, lauramide monoisopropanolamine, tallowamide monoethanolamine, isostearamide diethanolamine, isostearamide monoethanolamine) and mixtures thereof.

Preferably, the hair conditioner formulation of the present invention further comprises a thickener. More preferably, the hair conditioner formulation of the present invention further comprises a thickener, wherein the thickener is selected to increase the viscosity of the hair conditioner formulation, preferably without substantially modifying the other properties of the hair conditioner formulation. Preferably, the hair conditioner formulation of the present invention further comprises a thickener, wherein the thickener is selected to increase the viscosity of the hair conditioner formulation, preferably without substantially modifying the other properties of the hair conditioner formulation and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the hair conditioner formulation.

Preferably, the hair conditioner formulation of the present invention further comprises an antimicrobial agent/preservative. More preferably, the hair conditioner formulation of the present invention further comprises an antimicrobial/preservative, wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Most preferably, the hair conditioner formulation of the present invention, further comprises an antimicrobial/preservative, wherein the antimicrobial/preservative is a mixture of phenoxyethanol and an isothiazolinone (more preferably, wherein the antimicrobial/preservative is a mixture of phenoxyethanol and methylisothiazolinone).

Preferably, the hair conditioner formulation of the present invention optionally further comprises a pH adjusting agent. More preferably, the hair conditioner formulation of the present invention, further comprises a pH adjusting agent, wherein the hair conditioner formulation has a pH of 4 to 9 (preferably, 4.25 to 8; more preferably, 4.5 to 7; most preferably, 4.75 to 6).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes citric acid. Most preferably, the pH adjusting agent is citric acid.

Preferably, the method of conditioning mammalian hair of the present invention comprises: selecting a hair conditioner formulation of the present invention and applying the hair conditioner formulation to mammalian hair. Preferably, the method of conditioning mammalian hair of the present invention, further comprises: wetting the hair with water before applying the hair conditioner. Most preferably, the method of conditioning mammalian hair of the present invention, comprises: selecting a hair conditioner formulation of the present invention; wetting mammalian hair; and applying the hair conditioner formulation to the wetted mammalian hair.

Some embodiments of the present invention will now be described in detail in the following Examples.

Synthesis S1: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (125.97 g; 21.4% Polydex aqueous dextran), N,N-dimethyloctylamine (9.83 g) and epichlorohydrin (5.69 g). The contents of the flask were stirred at 70 rpm. While stirring, the head space in the flask was purged with a slow, steady flow of nitrogen (about one bubble per second) for one hour to remove any entrained oxygen in the apparatus.

After the one hour nitrogen purge, heat was applied to the flask contents using a heating mantle and the J-KEM controller (set-point of 70° C.). While stirring under nitrogen, the flask contents were maintained at 70° C. for 5 hours. During this time, the color of the flask contents changed from yellow to dark brown, and the viscosity noticeably increased as the reaction progressed.

The flask contents were then cooled in a water bath while maintaining a positive nitrogen pressure in the flask. A solid polymer product was recovered from the flask contents by non-solvent precipitation with acetone. A Waring blender was charged with 500 mL of acetone and approximately 20 mL of polymer solution was slowly and continuously added at moderate mixing speed using a plastic disposable syringe. The polymer was recovered by vacuum filtration through a Buchner funnel with a fine frit. The Waring blender was charged with fresh acetone and the non-solvent precipitation of the remaining aqueous solution was continued. The polymer was briefly air dried, then dried overnight in vacuo at 50° C. The dried polymer was manually ground with a mortar and pestle, and screened through a US standard #30 sieve.

The product polymer was obtained as a white solid (29.63 g), with a volatiles content of 2.47%, and ash content (as sodium chloride) of 1.84%, and a Kjeldahl nitrogen content (corrected for ash and volatiles) of 1.442%, corresponding to a CS value of 0.225.

Synthesis S2: Synthesis of Cationic Dextran Polymer

A 500 mL, four necked, round bottom flask fitted with a rubber serum cap, a nitrogen inlet, a pressure equalizing addition funnel, a stirring paddle and motor, a subsurface thermocouple connected to a J-KEM controller and a Friedrich condenser connected to a mineral oil bubbler was charged with dextran polymer (126.92 g; 21.4% Polydex aqueous dextran), N,N-dimethyldodecylamine (13.54 g) and epichlorohydrin (5.84 g). The contents of the flask were stirred at 70 rpm. While stirring, the head space in the flask was purged with a slow, steady flow of nitrogen (about one bubble per second) for one hour to remove any entrained oxygen in the apparatus.

After the one hour nitrogen purge, heat was applied to the flask contents using a heating mantle and the J-KEM controller (set-point of 70° C.). While stirring under nitrogen, the flask contents were maintained at 70° C. for 5 hours. During this time, the color of the flask contents changed from yellow to dark brown, and the viscosity noticeably increased as the reaction progressed.

The flask contents were then cooled in a water bath while maintaining a positive nitrogen pressure in the flask. A solid polymer product was recovered from the flask contents by non-solvent precipitation with acetone. A Waring blender was charged with 500 mL of acetone and approximately 20 mL of polymer solution was slowly and continuously added at moderate mixing speed using a plastic disposable syringe. The polymer was recovered by vacuum filtration through a Buchner funnel with a fine frit. The Waring blender was charged with fresh acetone and the non-solvent precipitation of the remaining aqueous solution was continued. The polymer was briefly air dried, then dried overnight in vacuo at 50° C. The dried polymer was manually ground with a mortar and pestle, and screened through a US standard #30 sieve.

The product polymer was obtained as a white solid (29.96 g), with a volatiles content of 2.35%, and ash content (as sodium chloride) of 1.99%, and a Kjeldahl nitrogen content (corrected for ash and volatiles) of 1.079%, corresponding to a CS value of 0.163.

Comparative Examples CF1-CF2 and Examples F1-F2: Hair Conditioner Formulations A hair conditioner formulation was prepared in each of Comparative Examples CF1-CF2 and Examples F1-F2 having the formulation noted in Table 1.

TABLE 1

| Ingredient INCI name | CF1 wt % | CF2 wt % | F1 wt % | F2 wt % |
|---|---|---|---|---|
| Deionized water | q.s. 100 | | | |
| Hydroxyethyl cellulose[1] | 1.4 | 1.4 | 1.4 | 1.4 |
| Tetrasodium EDTA[2] | 0.2 | 0.2 | 0.2 | 0.2 |
| Cetearyl alcohol[3] | 1 | 1 | 1 | 1 |
| Glyceryl stearate (and) PEG-100 stearate[4] | 1 | 1 | 1 | 1 |
| Unmodified branched chain dextran[5] | 0 | 0.3 | 0 | 0 |
| Polymer product of Synthesis S1 | 0 | 0 | 0.3 | 0 |
| Polymer product of Synthesis S2 | 0 | 0 | 0 | 0.3 |
| Phenoxyethanol and Methylisothiazolinone[6] | 0.5 | 0.5 | 0.5 | 0.5 |

[1]available from The Dow Chemical Company under tradename Cellosize ™ PCG-10
[2]available from The Dow Chemical Company under tradename Versene ™ 220
[3]available from Croda Inc. under tradename Crodacol ™ CS50
[4]available from Croda Inc. under tradename Arlacel ™ 165
[5]available from Sigma Aldrich under catalog number D4876
[6]preservative available from The Dow Chemical Company under tradename Neolone ™ PE

Hair Conditioning Performance

Studies to evaluate ease of wet and dry combing of hair treated with a rinse off conditioner formulation of Comparative Examples CF1-CF2 and Examples F1-F2 were performed as follows. Slightly bleached Caucasian hair from International Hair Importers was used for testing the conditioners. Each tress weighed 2 grams. Each tress was rinsed for 30 seconds under a stream of 40° C. tap water. Using a pipette, 0.4 grams of a solution containing nine percent of sodium lauryl sulfate was applied and lathered through each tress for 30 seconds. The tresses were then rinsed for 1 minute under running water. Excess water was removed from the tresses by passing each tress between the index and middle fingers of the hand. The tresses were then treated with a rinse off conditioner formulation of Comparative Examples CF1-CF2 and Examples F1-F2 at 0.4 g formulation/g of hair by massaging the formulation into the wet/damp hair for 1 minute. The tresses were rinsed for 30 seconds under running water and dried overnight at room temperature.

An INSTRON Model 4464 running BlueHill 2 software was also used for determining conditioning performance by the ease of wet combing and the ease of dry combing. The test employed an INSTRON strain gauge, which was equipped to measure the force required to comb the hair. The conditioning performance was based on the ability of the rinse off conditioner formulation, to reduce the force required to comb the hair with the INSTRON strain gauge. The force was reported as an Average Combing Load (ACL). The lower the number of the ACL value, the better the conditioning effect imparted by the rinse off conditioner formulation tested.

According to the INSTRON wet combing method, hair was first wetted by dipping into distilled water, and then the hair was detangled by combining the tress three times. The tress was then retangled by dipping in distilled water three times. Excess water was removed by passing the tress through the index and middle fingers of the hand twice. The tress was placed on a hanger and INSTRON combed. An average wet combing force from three tresses was measured for each rinse off conditioner formulation. The average wet combing results are provided in Table 2.

According to the INSTRON dry combining method, dry hair was detangled by combining the tress 3 times. Then the hair was retangled by swirling the tress clockwise 3 times and swirling it counter clockwise 3 times. The tress was then placed on a hanger and INSTRON combed. An average dry combining force from three tresses was measured for each rinse off conditioner formulation. The average dry combining results are provided in Table 2.

TABLE 2

| Rinse off Conditioner | ACL (kgf) Dry | Wet |
|---|---|---|
| Comparative Example CF1 | 0.0463 | 0.868 |
| Comparative Example CF2 | 0.0636 | 0.762 |
| Example F1 | 0.0263 | 0.221 |
| Example F2 | 0.0284 | 0.195 |

Hair Hydrophobicity

Rinse off hair conditioner prepared according to each of Comparative Example CF2 and Example F2 were tested on two separate 3 g hair samples (Slightly Bleached Caucasian Hair, International Hair Importers, Inc.). The hair samples were first rinsed with water for 30 seconds. Then a 9% w/w aqueous solution of sodium lauryl sulfate was massaged into the hair samples for 30 seconds. Then the hair samples were rinsed with water for 60 seconds. The hair samples were then treated with the rinse off hair conditioner at a dosage of 0.4 g/g or hair and massaged onto the hair for 30 seconds. The hair samples where then rinsed with water for 30 seconds and dried before hydrophobicity testing.

To measure hydrophobicity of the hair, the tresses were combed straight and then held tightly on both ends with a holder. Ten 30 μL drops of water were placed at different locations on each tress from the root to the tip. While the water was observed to immediately dissipate into the tress treated with the formulation of Comparative Example CF2, the water continued to bead off of the tress treated with the formulation of Example F2 even after 5 minutes indicating that the rinse off conditioner formulation of Example F2 successfully restored hydrophobicity benefit to the slightly bleached Caucasian hair.

Comparative Examples CF3-CF4 and Example F3: Hair Conditioning Shampoo

A hair conditioning shampoo formulation was prepared in each of Comparative Examples CF3-CF4 and Example F3 having the formulation noted in Table 3.

TABLE 3

| Ingredient INCI name | CF3 wt % | CF4 wt % | F3 wt % |
|---|---|---|---|
| Deionized water | | q.s. 100 | |
| Sodium lauryl ether sulfate[1] | 9.0 | 9.0 | 9.0 |
| Tetrasodium EDTA[2] | 0.2 | 0.2 | 0.2 |
| Cocamide MEA[3] | 1.0 | 1.0 | 1.0 |
| Cocamidopropyl Betaine[4] | 2.1 | 2.1 | 2.1 |
| Guar hydroxypropyltrimonium chloride[5] | 0 | 0.3 | 0 |
| Polymer product of Synthesis S2 | 0 | 0 | 0.3 |
| Phenoxyethanol and Methylisothiazolinone[76] | 0.25 | 0.25 | 0.25 |
| PEG-150 Pentaerythrityl Tetrastearate[7] | | q.s. viscosity 11,000 cP | |
| Sodium hydroxide or Citric acid | | q.s. pH 5 | |

[1]available from Stepan Company under tradename Steol ® CS-130
[2]available from The Dow Chemical Company under tradename Versene ™ 220
[3]available from Croda Inc. under tradename Incromide ™ CMEA
[4]available from Stepan Company under tradename Amphosol ® CA
[5]available from Solvay Novecare under tradename Jaguar Excel
[6]preservative available from The Dow Chemical Company under tradename Neolone ™ PE
[7]available from Croda Inc. under tradename Crothix ™-PA-(MH)

Hair Conditioning Performance

Studies to evaluate ease of wet and dry combing of hair treated with conditioning shampoo formulation of Comparative Examples CF3-CF4 and Example F3 were performed as follows. Slightly bleached Caucasian ("SBC") hair and Virgin brown ("VB") hair from International Hair Importers were used for the testing. Each tress weighed 2 grams. Each tress was rinsed for 15 seconds under a stream of 40° C. tap water. Using a pipette, 0.2 grams of a solution containing nine percent of sodium lauryl sulfate was applied and lathered through each tress for 30 seconds. The tresses were then rinsed for 1 minute under running water. Excess water was removed from the tresses by passing each tress between the index and middle fingers of the hand. The tresses were then treated with a conditioning shampoo formulation of Comparative Examples CF3-CF4 and Example F3 at 0.1 g formulation/g of hair by massaging the formulation into the wet/damp hair for 1 minute. The tresses were placed on a tray covered with paper towels and dried overnight at room temperature.

Wet combing results for hair tresses treated with the conditioning shampoo formulations of Comparative Examples CF3-CF4 and Example F3 were determined as follows. The hair tress was dipped one time in deionized water. Excess water was removed from the tress by pulling through the index and middle fingers twice. Each tress was then a combed until tangles were removed. Each tress was then retangled by dipping in distilled water three times at roughly once per second frequency. Excess water was removed by passing through the index and middle fingers twice. Then, with a comb in place on a Diastron MTT175 tensile tester with 50 g normal force mounted on rubber probe was used for testing in a temperature and humidity controlled room. Three tresses per treatment and four measurements per tress were tested to generate the total mean work in joules reported in Table 4.

TABLE 4

| Conditioning Shampoo Formulation | Hair | Total work (J) |
|---|---|---|
| Comparative Example CF3 | SBC | 0.85 |
| Comparative Example CF3 | VB | 0.33 |
| Comparative Example CF4 | SBC | 0.36 |
| Comparative Example CF4 | VB | 0.19 |
| Example F3 | SBC | 0.44 |
| Example F3 | VB | 0.20 |

We claim:

1. A hair conditioner formulation, comprising:
a dermatologically acceptable vehicle; and
a conditioning polymer, wherein the conditioning polymer is a cationic dextran polymer, comprising a dextran polymer functionalized with quaternary ammonium groups; wherein the dextran polymer has a weight average molecular weight of 50,000 to 3,000,000 Daltons; wherein the quaternary ammonium groups are selected from the group consisting of quaternary ammonium moieties of formula (A) bound to a pendent oxygen on the dextran polymer

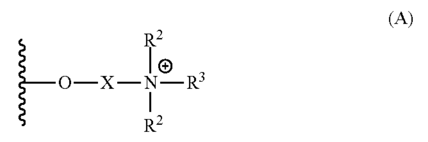

(A)

wherein

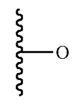

is a pendent oxygen on the dextran polymer; wherein X is a divalent linking group bonding the quaternary ammonium moiety to the pendent oxygen on the dextran polymer; wherein each $R^2$ is independently selected from the group consisting of a $C_{1-3}$ alkyl group; and wherein $R^3$ is selected from the group consisting of a linear or branched $C_8$ alkyl group and a linear or branched $C_{12}$ alkyl group.

2. The hair conditioner formulation of claim 1, wherein the hair conditioner formulation contains less than 0.01 wt %, based on the total weight of the hair conditioner formulation, of a dermatologically acceptable oil.

3. The hair conditioner formulation of claim 2, wherein the hair conditioner formulation contains less than 0.1 wt %, based on the total weight of the hair conditioner formulation, of silicon containing molecules.

4. The hair conditioner formulation of claim 3, wherein the hair conditioner formulation is selected from the group consisting of a leave on conditioner, a rinse off conditioner and a conditioning shampoo.

5. The hair conditioner formulation of claim 4, wherein the hair conditioner formulation is a leave on conditioner.

6. The hair conditioning formulation of claim 5, wherein the cationic dextran polymer has a Kjeldahl nitrogen content corrected for ash and volatiles, TKN, of 0.5 to 5.0 wt %.

7. The hair conditioning formulation of claim 6, wherein $R^3$ is a linear or branched $C_{12}$ alkyl group.

8. The hair conditioner formulation of claim 7, further comprising a thickener.

9. The hair conditioner formulation of claim 8, further comprising a preservative.

10. A method of conditioning mammalian hair, comprising:

selecting a hair conditioner formulation according to claim 1; and applying the hair conditioner formulation to mammalian hair.

* * * * *